(12) United States Patent
Watanabe et al.

(10) Patent No.: US 8,998,487 B2
(45) Date of Patent: Apr. 7, 2015

(54) X-RAY IMAGING APPARATUS

(71) Applicant: Canon Kabushiki Kaisha, Tokyo (JP)

(72) Inventors: Kazuhiro Watanabe, Tokyo (JP);
Hiroyuki Tokuda, Yokohama (JP);
Hitomi Ogasawara, Yokohama (JP);
Takashi Ogura, Tokyo (JP); Jun Murata, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 242 days.

(21) Appl. No.: 13/738,027

(22) Filed: Jan. 10, 2013

(65) Prior Publication Data

US 2013/0182828 A1    Jul. 18, 2013

(30) Foreign Application Priority Data

Jan. 17, 2012 (JP) .................. 2012-007385

(51) Int. Cl.
*G21K 5/04* (2006.01)
*A61B 6/00* (2006.01)
*G21K 1/00* (2006.01)
*A61B 6/06* (2006.01)

(52) U.S. Cl.
CPC .............. *A61B 6/4405* (2013.01); *G21K 1/00* (2013.01); *A61B 6/06* (2013.01)

(58) Field of Classification Search
CPC ............ H05G 1/00; H05G 1/02; H05G 1/04; H05G 1/06; G03B 42/02; G03B 42/021
USPC .................. 378/193, 195, 196, 197, 198, 203
See application file for complete search history.

(56) References Cited

U.S. PATENT DOCUMENTS

| | | | | |
|---|---|---|---|---|
| 5,638,420 | A * | 6/1997 | Armistead ...................... | 378/57 |
| 2010/0054422 | A1* | 3/2010 | Ohmura et al. ................ | 378/196 |
| 2012/0069960 | A1* | 3/2012 | Kitagawa et al. .............. | 378/41 |
| 2013/0188781 | A1 | 7/2013 | Kaku et al. ..................... | 378/197 |
| 2013/0230142 | A1 | 9/2013 | Murata et al. .................. | 378/62 |

FOREIGN PATENT DOCUMENTS

JP  2008-079728  4/2008
JP  2011-056170  3/2011

* cited by examiner

*Primary Examiner* — Nicole Ippolito
(74) *Attorney, Agent, or Firm* — Fitzpatrick, Cella, Harper & Scinto

(57) ABSTRACT

An X-ray imaging apparatus comprises an X-ray source; a housing configured to accommodate the X-ray source; and a plurality of supporting legs each connected to the housing via a movable connecting portion and configured to support the housing, wherein each of the supporting legs can change, by the movable connecting portion, a support angle made by a ground plane and the supporting leg.

7 Claims, 8 Drawing Sheets

F I G. 1
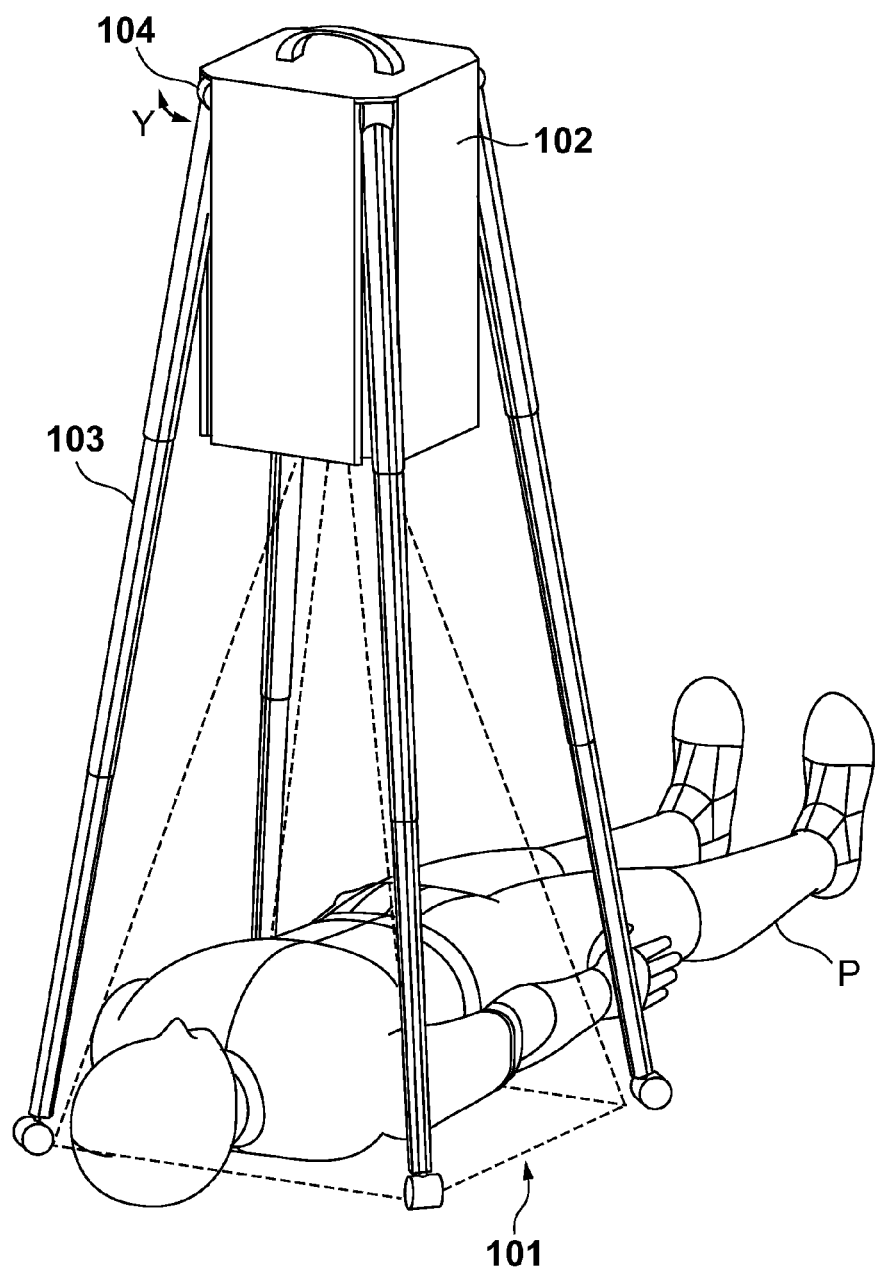

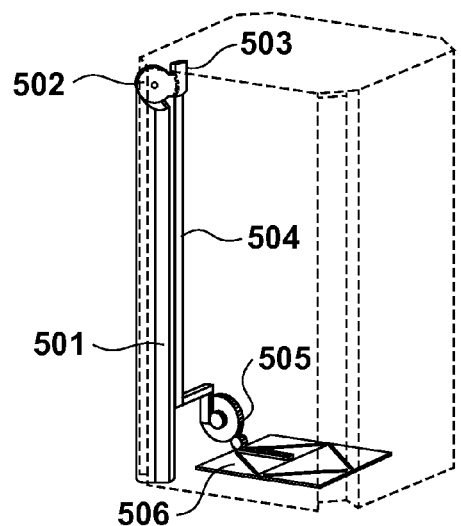
F I G. 5A
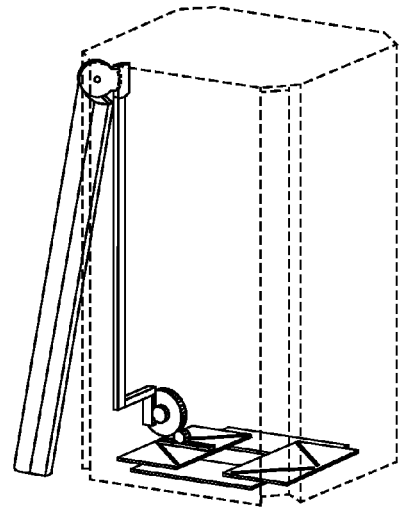
F I G. 5B
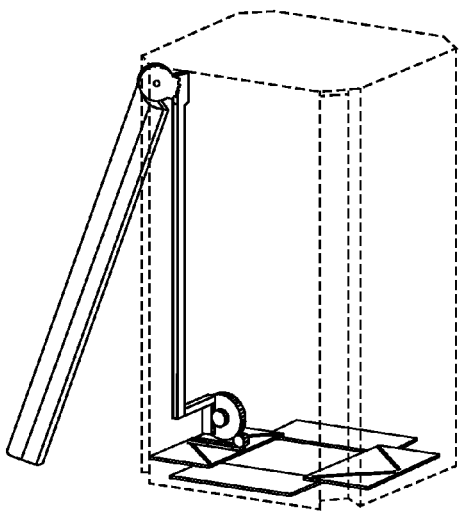
F I G. 5C

X-RAY IMAGING APPARATUS

BACKGROUND OF THE INVENTION

1. Field of the Invention

The present invention relates to an X-ray imaging apparatus.

2. Description of the Related Art

In recent years, X-ray imaging aiming at medical diagnosis or the like is used in emergency treatment, at a site of disaster, or the like by reducing the size and weight of an X-ray imaging apparatus including an X-ray source and increasing the portability. Japanese Patent Laid-Open No. 2011-56170 discloses a technique of using an X-ray imaging apparatus vertically hung above the inspection part of an object by a collapsible holder. Japanese Patent Laid-Open No. 2008-79728 discloses an X-ray imaging apparatus including an X-ray shield member that restricts the irradiation range of X-rays emitted by an X-ray source to irradiate an object, and a driving unit that is connected to the X-ray shield member to increase/decrease the X-ray shield area of the X-ray shield member.

However, the X-ray imaging apparatus as disclosed in Japanese Patent Laid-Open No. 2011-56170 necessitates labor and time for assembly and installation of the holder at the time of X-ray imaging. In addition, there is a problem of portability because the X-ray imaging apparatus and the holder are separate. The X-ray imaging apparatus as disclosed in Japanese Patent Laid-Open No. 2008-79728 can neither improve the portability nor facilitate installation.

SUMMARY OF THE INVENTION

In consideration of the above-described problems, the present invention provides an X-ray imaging apparatus that has high portability and is easy to install.

According to one aspect of the present invention, there is provided an X-ray imaging apparatus comprising: an X-ray source; a housing configured to accommodate the X-ray source; and a plurality of supporting legs each connected to the housing via a movable connecting portion and configured to support the housing, wherein each of the supporting legs can change, by the movable connecting portion, a support angle made by a ground plane and the supporting leg.

Further features of the present invention will be apparent from the following description of exemplary embodiments with reference to the attached drawings.

BRIEF DESCRIPTION OF THE DRAWINGS

FIG. 1 is a perspective view showing the schematic arrangement of an X-ray imaging apparatus according to the first embodiment;

FIGS. 5A to 5C are perspective views showing the schematic arrangement of an X-ray imaging apparatus according to the third embodiment;

DESCRIPTION OF THE EMBODIMENTS

Figure 2A:
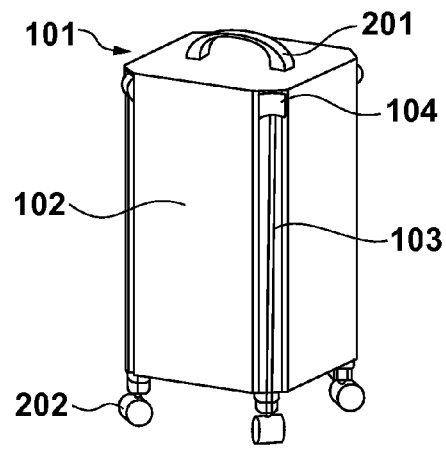
FIG. 2A is a perspective view showing the form of the X-ray imaging apparatus according to the first embodiment at the time of transport.

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

(First Embodiment)

The schematic arrangement of an X-ray imaging apparatus according to the first embodiment will be described with reference to FIG. 1. An X-ray imaging apparatus 101 includes a housing 102 that accommodates an X-ray source, and a plurality of supporting legs 103. The X-ray source generates X-rays for medical diagnosis and irradiates an object P with them. The X-ray source generally uses, for example, an X-ray tube that irradiates an X-ray target made of a bulk metal with thermoelectrons emitted by a filament heated to a high temperature so as to generate X-rays on the electron beam incident side, and irradiates the object P with the X-rays. The X-rays that have passed through the object P are detected by an X-ray detection sensor (not shown) installed facing the X-ray source, and output as an electrical signal. This electrical signal undergoes image processing to obtain a so-called X-ray image.

The supporting legs 103 stand on the ground or floor surface and support the housing 102 above the object P. Note that FIG. 1 illustrates an example in which the supporting legs 103 include four legs. However, even two legs can stand and support if they have a predetermined ground width, and the number of legs is not limited.

The X-ray imaging apparatus 101 may further include movable connecting portions 104 that rotatably connect the housing 102 to the supporting legs 103. The supporting legs 103 may be configured to be rotatable by the movable connecting portions 104 in a direction indicated by an arrow Y. This allows the support angles of the supporting legs 103 to be changed in accordance with the size and the like of the object (patient). Note that the support angle is the angle made by the ground (ground plane) and the supporting leg 103. The supporting legs 103 may be configured to be able to stretch/contract along the longitudinal direction. Even if the supporting legs 103 cannot stretch/contract, the X-ray imaging apparatus can easily be transported in a state in which the support angles are set to 180° (that is, in a state in which the supporting legs 103 are opened to direct the ends vertically upward). After the transport, the X-ray imaging apparatus can easily be installed by directing the ends of the supporting legs 103 vertically downward.

Figure 2B:
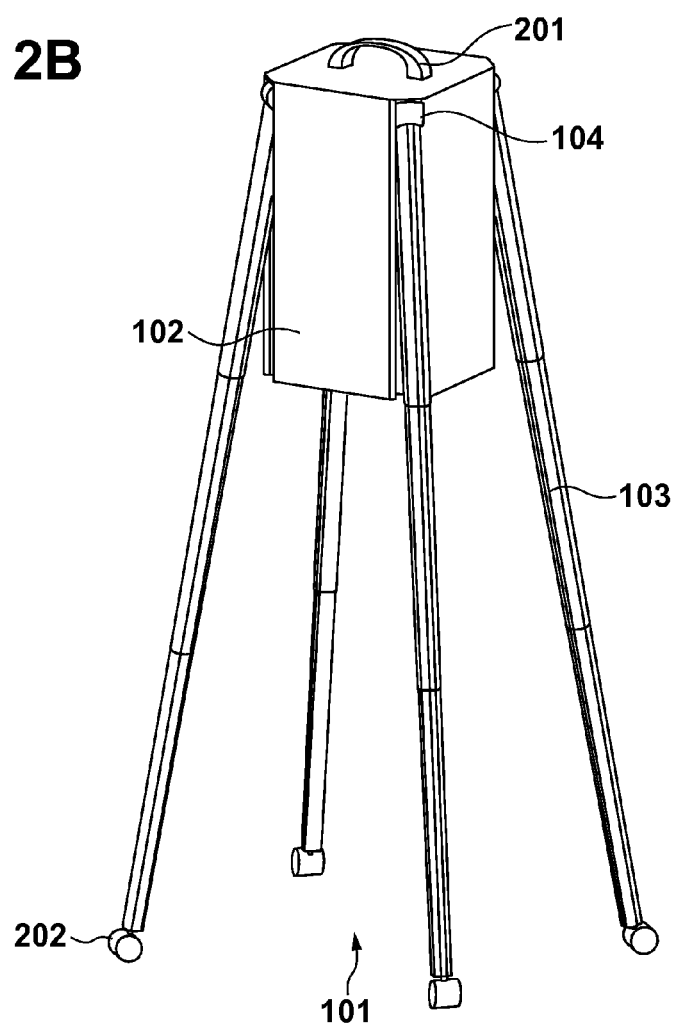
FIG. 2B is a perspective view showing the form of the X-ray imaging apparatus according to the first embodiment at the time of installation and use (at the time of X-ray imaging)

The transition of the X-ray imaging apparatus according to the first embodiment from the form at the time of transport to the form at the time of installation/use (X-ray imaging) will be described with reference to FIGS. 2A and 2B. As shown in FIGS. 2A and 2B, the X-ray imaging apparatus 101 may further include a handle 201 and caster portions 202 that make the X-ray imaging apparatus movable on the ground plane. The supporting legs 103 are configured to be able to stretch/contract.

As shown in FIG. 2A, at the time of transport, the user contracts the supporting legs 103. At this time, the supporting legs 103 are in contact with the vertical sides of the housing 102. The user can carry the X-ray imaging apparatus by the handle 201, or move on the ground plane by unlocking the caster portions 202 at the ends of the supporting legs and dragging the X-ray imaging apparatus.

As shown in FIG. 2B, at the time of installation/use (X-ray imaging) in emergency treatment, at a site of disaster, or the like, the user can lock the caster portions 202 and stretch the supporting legs 103 to increase the support angles via the movable connecting portions 104.

According to this embodiment, since no separate holder is needed for installing the X-ray source, the portability is improved. At the time of use (X-ray imaging), the X-ray imaging apparatus can easily and quickly be installed by the operation of stretching the supporting legs and increasing the support angles. The operation of locking the casters enables the X-ray imaging apparatus to be stationarily installed and the installation to be further facilitated.

(Second Embodiment)

Figure 3A:
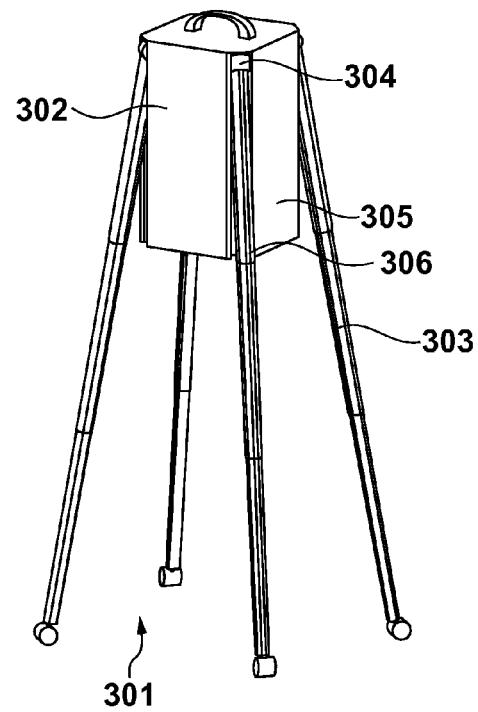
FIGS. 3A and 3B are perspective views showing the schematic arrangement of an X-ray imaging apparatus according to the second embodiment.
Figure 3B:
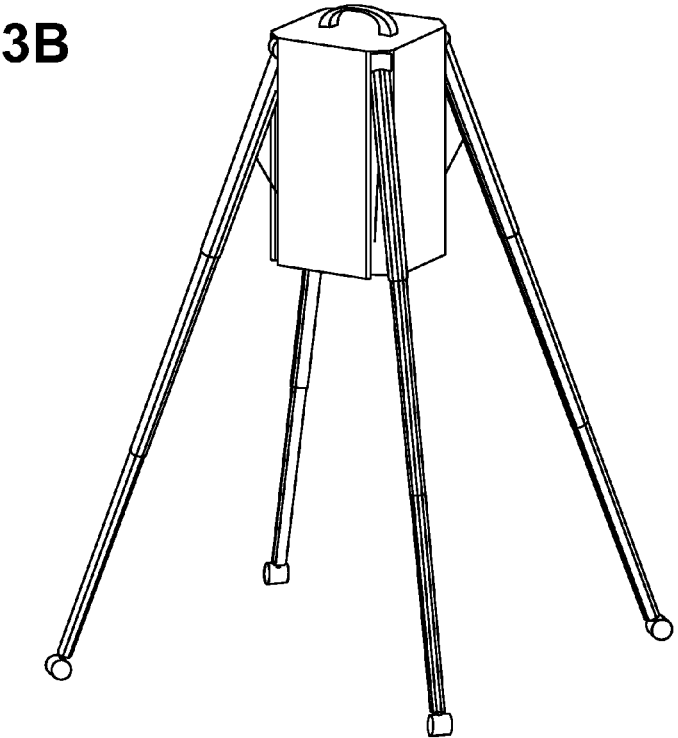

In the second embodiment, the X-ray irradiation range is changed in accordance with the support angles of the supporting legs. The schematic arrangement of an X-ray imaging apparatus according to the second embodiment will be described with reference to FIGS. 3A and 3B. FIG. 3A illustrates a state in which the supporting legs are closed (the support angles are large), and FIG. 3B illustrates a state in which the supporting legs are opened (the support angles are small).

An X-ray imaging apparatus 301 further includes X-ray shield members 305 and interlock mechanisms 306 in addition to a housing 302 that accommodates an X-ray source, supporting legs 303, and movable connecting portions 304.

The X-ray shield members 305 are used to restrict the irradiation range of X-rays emitted by the X-ray source to a predetermined range. The interlock mechanisms 306 interlock the operations of the supporting legs 303 with those of the X-ray shield members 305 so as to change the X-ray irradiation range in accordance with the support angles of the supporting legs. X-rays radially emitted by the X-ray source irradiate an object (patient) after their irradiation field has been restricted by the X-ray shield members 305 into, for example, a rectangular shape. The support angles of the supporting legs 303 can be changed by the movable connecting portions 304 in accordance with the size and the like of the object (patient). When the support angles of the supporting legs 303 are changed, the interlock mechanisms 306 move the positions of the X-ray shield members 305 and adjust the X-ray irradiation range.

Figure 4A:
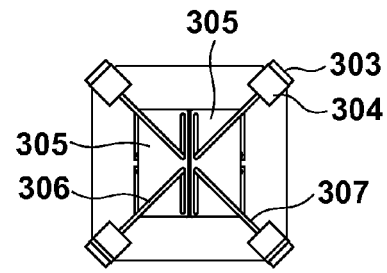
FIGS. 4A to 4C are see-through sectional views showing the X-ray imaging apparatus according to the second embodiment viewed from the upper side.
Figure 4B:
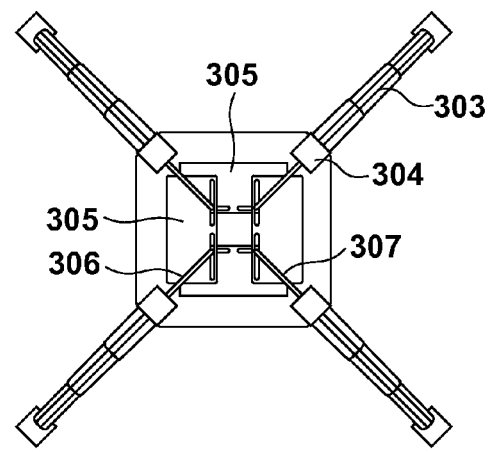
Figure 4C:
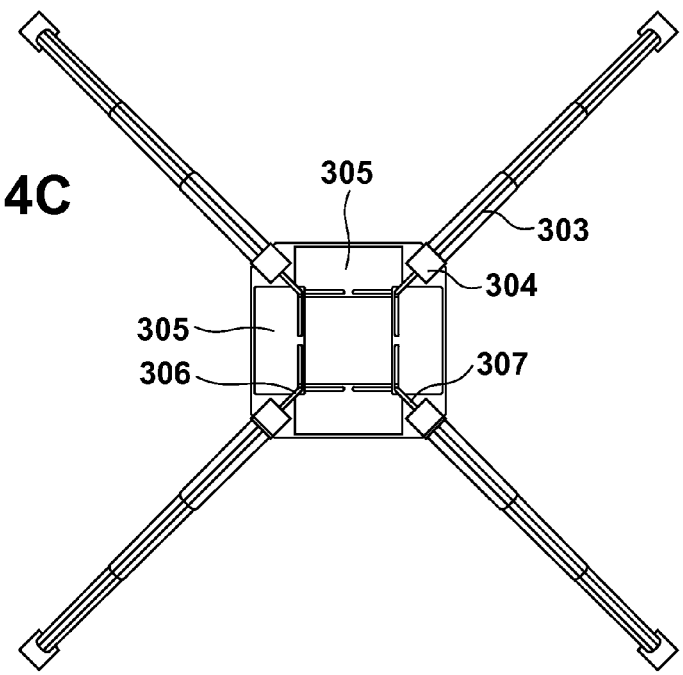

A state in which the interlock mechanisms 306 move the positions of the X-ray shield members 305 in accordance with the support angles of the supporting legs 303 and change the X-ray irradiation range will be described with reference to FIGS. 4A to 4C. FIGS. 4A to 4C are see-through sectional views of the X-ray imaging apparatus 301 viewed from the upper side. The X-ray shield members 305 are formed from four plate-shaped members made of a material such as lead or tungsten having an X-ray shielding capability. The plate-shaped members slide in parallel to the opening portion of the X-ray source and are connected to the supporting legs 303 via link mechanisms 307, respectively. For this reason, when the supporting legs 303 are closed (when the support angles are large), as shown in FIG. 4A, the plate-shaped members slide in directions to come close to each other and narrow the X-ray irradiation range. On the other hand, when the supporting legs 303 are opened (when the support angles are small), as shown in FIGS. 4B and 4C, the plate-shaped members slide in directions to move away from each other and widen the X-ray irradiation range.

According to this embodiment, it is possible to change the X-ray irradiation range to an appropriate range in accordance with the support angles of the supporting legs. When the object is large, the X-ray irradiation range can be widened by opening the supporting legs. Conversely, when the object is small, the X-ray irradiation range can be narrowed by closing the supporting legs. That is, it is possible to appropriately adjust the X-ray irradiation range in accordance with the size of the object and prevent unnecessary exposure.

(Third Embodiment)

In the third embodiment, the rotary motion of a movable connecting portion is converted into a linear movement and transferred via a gear and interlocked with the opening/closing operation of an X-ray shield member. The basic arrangement of the X-ray imaging apparatus is the same as in the first embodiment.

The opening/closing operation of the X-ray shield member in the X-ray imaging apparatus according to the third embodiment will be described with reference to FIGS. 5A to 5C. FIG. 5A corresponds to a state in which supporting legs 501 are closed (the support angles are large), and FIGS. 5B and 5C correspond to states in which the supporting legs 501 are opened (the support angles are small).

The X-ray imaging apparatus according to the third embodiment includes a transfer mechanism 510. The transfer mechanism 510 includes a gear 503, a transfer unit 504, and an opening/closing transfer unit 505 and interlocks the support angle of the supporting leg 501 and the position of an X-ray shield member 506.

When the support angle of the supporting leg 501 is changed, the rotary motion of a movable connecting portion 502 is transferred to the transfer unit 504 via the gear 503 as a linear movement. The transfer unit 504 is formed from a rod, a belt, a chain, or the like, transfers the rotary motion of the movable connecting portion 502, and interlocks the rotary motion with the opening/closing operation of the X-ray shield member 506. The opening/closing transfer unit 505 further changes the direction of the linear movement transferred by the transfer unit 504 and adjusts the position of the X-ray shield member 506 connected to the opening/closing transfer unit 505. The X-ray shield members 506 are thus opened/closed.

According to this embodiment, it is possible to change the X-ray irradiation range to an appropriate range in accordance with the support angles of the supporting legs. When the object is large, the X-ray irradiation range can be widened by opening the supporting legs. Conversely, when the object is small, the X-ray irradiation range can be narrowed by closing the supporting legs. That is, it is possible to appropriately adjust the X-ray irradiation range in accordance with the size of the object and prevent unnecessary exposure.

(Fourth Embodiment)

Figure 6:
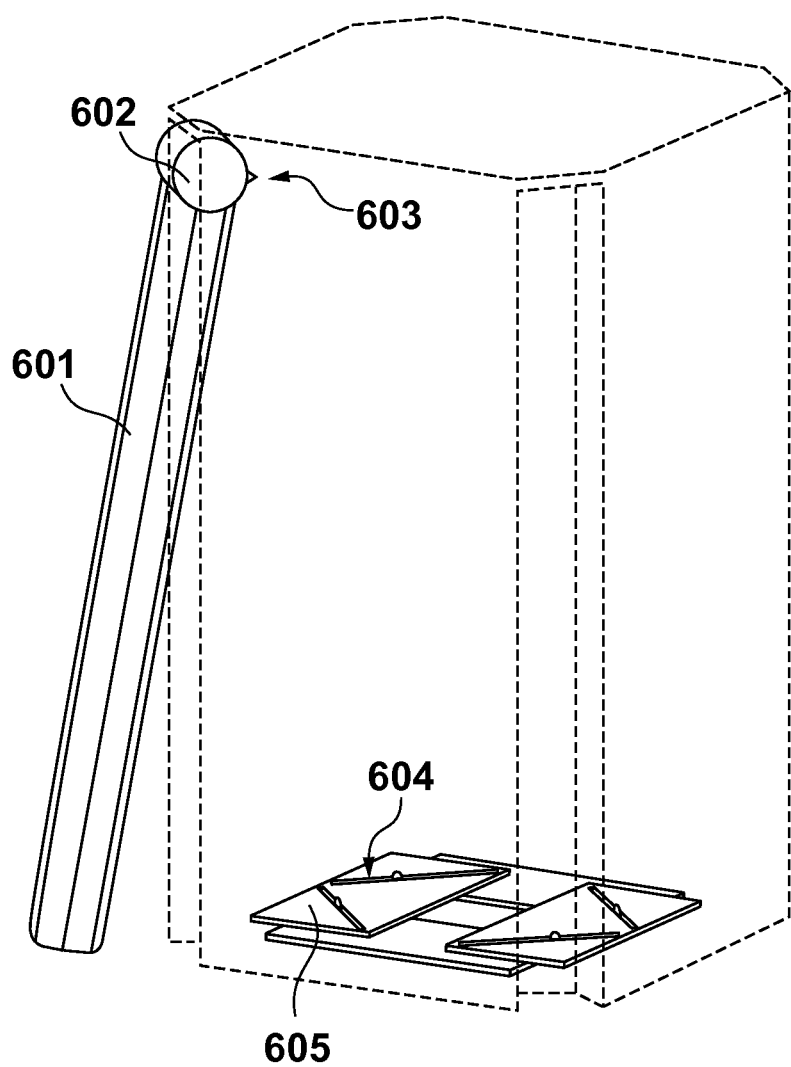
FIG. 6 is an explanatory view of opening/closing control in an X-ray imaging apparatus according to the fourth embodiment.

In the fourth embodiment, a support angle sensor detects the support angle of a supporting leg, thereby electrically controlling opening/closing of an X-ray shield member X. The basic arrangement of the X-ray imaging apparatus is the same as in the first embodiment. Electrical control of the opening/closing operation of the X-ray shield member will be explained with reference to FIG. 6. When the support angle of a supporting leg 601 is changed, a support angle sensor 603 detects the change in the support angle. An opening/closing control unit 604 opens/closes an X-ray shield member 605 in accordance with the angle detected by the support angle sensor 603. As for specific processing, first of all a detected angle that was detected by the support angle sensor 603 is transmitted to the opening/closing control unit 604 in an electronic signal. The opening/closing control unit 604, having received the detected angle, sends a driving signal to a motor arranged in order to open or close the X-ray shield member 605, thereby opening or closing the X-ray shield member 605. According to the above control, the larger the detection angle detected by the support angle sensor 603, the more the X-ray shield member 605 is opened.

According to this embodiment, it is possible to change the X-ray irradiation range to an appropriate range in accordance with the support angles of the supporting legs. When the object is large, the X-ray irradiation range can be widened by opening the supporting legs. Conversely, when the object is small, the X-ray irradiation range can be narrowed by closing the supporting legs. That is, it is possible to appropriately adjust the X-ray irradiation range in accordance with the size of the object and prevent unnecessary exposure. In addition, the electrical control allows the number of physical constituent elements to be decreased and in turn the weight to be reduced, resulting in higher portability.

(Fifth Embodiment)

Figure 7:
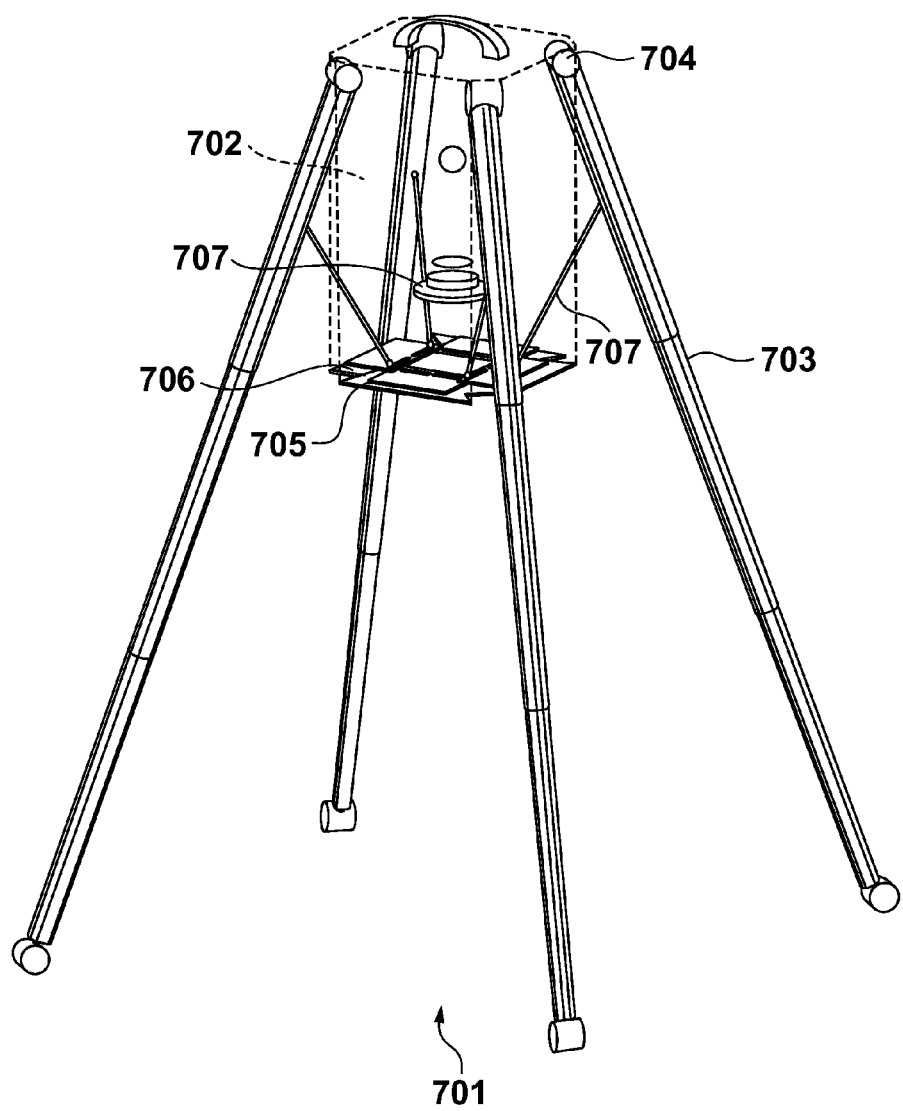
FIG. 7 is a perspective view showing the schematic arrangement of an X-ray imaging apparatus according to the fifth embodiment.

In the fifth embodiment, the X-ray irradiation range almost equals a range surrounded by the ground points where the supporting legs ground. The schematic arrangement of an X-ray imaging apparatus according to the fifth embodiment will be described with reference to FIG. 7. An X-ray imaging apparatus 701 includes a housing 702 that accommodates an X-ray source, supporting legs 703, movable connecting portions 704, X-ray shield members 705, interlock mechanisms 706, and a condenser optical system 707. The interlock mechanisms 706 interlock the operations of the supporting legs 703 with those of the X-ray shield members 705 so as to change the X-ray irradiation range in accordance with the support angles of the supporting legs 703.

The condenser optical system 707 condenses X-rays emitted by an X-ray tube or the like. The condenser optical system 707 can use an optical system formed from a convex lens, a Fresnel lens, and the like, an optical system using a concave mirror, or an optical system formed by combining them.

Figure 8:
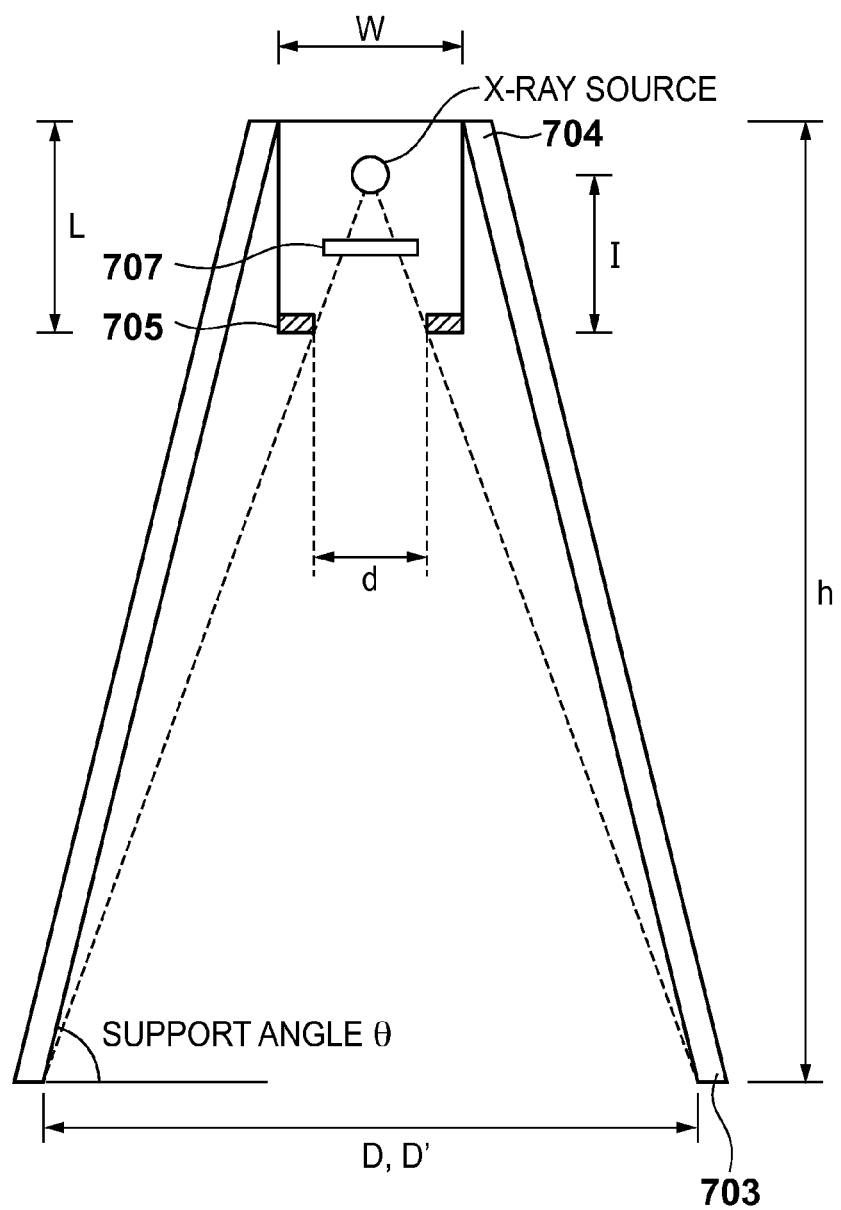
FIG. 8 is an explanatory view of the X-ray irradiation range of the X-ray imaging apparatus according to the fifth embodiment.

The X-ray irradiation range of the X-ray imaging apparatus according to the fifth embodiment will be described next with reference to FIG. 8. Let h be the height from the ground plane to the upper end of the X-ray imaging apparatus 701, I be the distance from the X-ray shield members 705 to the X-ray source, L be the height of the housing portion of the X-ray imaging apparatus 701, and d be the gap between the X-ray shield members 705. Note that when the condenser optical system 707 is provided, X-rays are condensed, and the distance I is an apparent distance different from the actual distance from the X-ray shield members 705 to the X-ray source.

The triangle having the X-ray source and the ends of the X-ray irradiation range as vertices is similar to the triangle having the X-ray source and the ends of the X-ray shield members 705 as vertices. For this reason, an irradiation range D on the ground plane is given by $$D = d \cdot (h + I - L)/I$$

On the other hand, letting H be the length of the supporting leg 703, θ be the support angle, and W be the width of the housing portion of the X-ray imaging apparatus 701 (the attachment interval of the supporting legs 703), a ground interval D' is given by $$D' = W + 2H \cos\theta$$

Since h = H sin θ, when the gap d between the X-ray shield members 705 with respect to the support angle θ satisfies $$d = (W + 2H \cos\theta) \cdot I/(H \sin\theta + I - L)$$

the irradiation range D on the ground plane equals the ground interval D'.

That is, when the gap d between the X-ray shield members is set to be almost equal to or smaller than $(W+2H\cos\theta)\cdot I/(H\sin\theta+I-L)$, the X-ray irradiation range can be configured to almost equal the range surrounded by the ground points where the supporting legs 703 ground and be arranged inside the range.

This allows the user such as a doctor or an X-ray technician to clearly know the X-ray irradiation range and properly align the X-ray imaging target area with the X-ray irradiation range. In addition, the safety is improved because the user can avoid exposure by refraining from entering the range where the supporting legs ground.

According to the present invention, it is possible to provide an X-ray imaging apparatus that has high portability and is easy to install.

(Other Embodiments)

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-007385 filed on Jan. 17, 2012, which is hereby incorporated by reference herein in its entirety.

What is claimed is:

1. An X-ray imaging apparatus comprising:
an X-ray source;
a housing configured to accommodate said X-ray source; and
at least four supporting legs each connected to said housing via a movable connecting portion and configured to support said housing,
wherein each of said supporting legs can change, by said movable connecting portion, a support angle made by a ground plane and said supporting leg and can stretch and contract along a longitudinal direction of said supporting leg,
wherein contracting each of said supporting legs and bringing each of said supporting legs into contact with said vertical side of said housing by decreasing the support angle of said movable connecting portion places the X-ray imaging apparatus into a compact configuration for transport, and wherein stretching each of said supporting legs and increasing the support angle of said movable connecting portions places the X-ray imaging apparatus in a configuration for use for imaging.

2. The apparatus according to claim 1, wherein each of said supporting legs includes, at an end in contact with the ground plane, a caster portion movable on the ground plane.

3. The apparatus according to claim 1, further comprising:
X-ray shield members configured to adjust an X-ray irradiation range to irradiate an object; and
link mechanisms configured to connect said supporting legs to said X-ray shield members, respectively,
wherein the X-ray irradiation range is adjusted by changing positions of said link mechanisms in accordance with changes in the support angles of said supporting legs and changing the positions of said X-ray shield members in accordance with the changes in the positions of said link mechanisms.

4. The apparatus according to claim 1,
wherein said movable connecting portion is rotatable in accordance with the change in the support angle of said supporting leg,
wherein the X-ray imaging apparatus further comprises:
X-ray shield members configured to adjust an X-ray irradiation range to irradiate an object; and
transfer mechanisms each configured to convert a rotary motion of a respective one of said movable connecting portions into a linear movement and move a position of a corresponding one of said X-ray shield members in accordance with the linear movement, and
wherein said transfer mechanism changes the position of said X-ray shield member and adjusts the X-ray irradiation range.

5. The apparatus according to claim 1, further comprising:
X-ray shield members configured to adjust an X-ray irradiation range to irradiate an object;
a support angle sensor configured to detect the support angle of each of said supporting legs; and
a control unit configured to control positions of said X-ray shield members in accordance with the support angles detected by said support angle sensor,
wherein said control unit controls the positions of said X-ray shield members and adjusts the X-ray irradiation range.

6. The apparatus according to claim 3, wherein the X-ray irradiation range is a range surrounded by four ground points where said supporting legs rest.

7. An X-ray imaging apparatus comprising:
an X-ray source;
a housing configured to accommodate said X-ray source;
a plurality of supporting legs each connected to said housing via a movable connecting portion and configured to support said housing;
X-ray shield members configured to adjust an X-ray irradiation range to irradiate an object; and
transfer mechanisms each configured to transfer a rotary motion of a respective one of said movable connecting portions to said X-ray shield members,
wherein each of said supporting legs can change, by said movable connecting portion, a support angle made by a ground plane and said supporting leg, and
wherein the rotary motion is interlocked with an opening/closing operation of said X-ray shield members.

* * * * *